(12) United States Patent
Manneck et al.

(10) Patent No.: US 10,667,998 B2
(45) Date of Patent: Jun. 2, 2020

(54) ODOR-REDUCED BLEACHING

(71) Applicant: Henkel AG & Co. KGaA, Duesseldorf (DE)

(72) Inventors: Hartmut Manneck, Barnitz (DE); Stefan Hoepfner, Hamburg (DE); Matthias Schweinsberg, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 103 days.

(21) Appl. No.: 16/063,655

(22) PCT Filed: Dec. 1, 2016

(86) PCT No.: PCT/EP2016/079380
§ 371 (c)(1),
(2) Date: Jun. 18, 2018

(87) PCT Pub. No.: WO2017/108363
PCT Pub. Date: Jun. 29, 2017

(65) Prior Publication Data
US 2018/0369088 A1    Dec. 27, 2018

(30) Foreign Application Priority Data

Dec. 21, 2015   (DE) .................. 10 2015 226 170

(51) Int. Cl.
| | | |
|---|---|---|
| *A61Q 5/06* | (2006.01) | |
| *A61K 8/25* | (2006.01) | |
| *A61K 8/26* | (2006.01) | |
| *A61Q 5/08* | (2006.01) | |
| *A61K 8/73* | (2006.01) | |
| *A61Q 5/10* | (2006.01) | |
| *A61K 8/19* | (2006.01) | |
| *A61K 8/04* | (2006.01) | |
| *A61K 8/22* | (2006.01) | |
| *A61K 8/81* | (2006.01) | |

(52) U.S. Cl.
CPC ............... *A61K 8/25* (2013.01); *A61K 8/042* (2013.01); *A61K 8/19* (2013.01); *A61K 8/22* (2013.01); *A61K 8/26* (2013.01); *A61K 8/73* (2013.01); *A61K 8/733* (2013.01); *A61K 8/8147* (2013.01); *A61K 8/8158* (2013.01); *A61Q 5/08* (2013.01); *A61Q 5/10* (2013.01); *A61K 2800/5426* (2013.01); *A61K 2800/884* (2013.01); *A61K 2800/95* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 4,660,580 A | | 4/1987 | Hoch et al. |
| 7,074,393 B2 * | | 7/2006 | Schmenger ............ A61K 8/044 424/62 |

FOREIGN PATENT DOCUMENTS

| | | |
|---|---|---|
| DE | 19756454 C1 | 6/1999 |
| DE | 102012223205 A1 | 6/2014 |
| EP | 0114414 A1 | 8/1984 |
| EP | 2574331 A2 | 4/2013 |
| WO | 9416672 A1 | 8/1994 |
| WO | 2007087978 A1 | 8/2007 |
| WO | 2014164213 A1 | 10/2014 |

OTHER PUBLICATIONS

EPO, International Search Report and Written Opinion issued in International Application No. PCT/EP2016/079380, dated Jan. 24, 2017.

* cited by examiner

Primary Examiner — Susan T Tran
(74) Attorney, Agent, or Firm — Lorenz & Kopf, LLP

(57) ABSTRACT

The subject matter of the present disclosure is a method for blonding and/or lightening keratinous fibers, which permits a multi-tone coloration with lighter ("highlights") sections (strands) to be produced, wherein the use of solid, flat separating aids, more particularly from solid materials, such as aluminum, paper or Styrofoam and similar materials, is not required. In addition, an entire keratinous fiber ensemble can be blonded and/or lightened, wherein the release of ammonia and the drying of the blonding or lightening agent are reduced.

16 Claims, No Drawings

ODOR-REDUCED BLEACHING

CROSS-REFERENCE TO RELATED APPLICATION

This application is a U.S. National-Stage entry under 35 U.S.C. § 371 based on International Application No PCT/EP2016/079380, filed Dec. 1, 2016 which was published under PCT Article 21(2) and which claims priority to German Application No. 10 2015 226 170.0, filed Dec. 21, 2015, which are all hereby incorporated in their entirety by reference.

TECHNICAL FIELD

In addition to dyeing, the lightening of one's own hair color and/or blonding is a very specific preference of many consumers, because a blond hair color is considered attractive and desirable from a fashion perspective. If keratin fibers are to be lightened or even bleached, the keratin fiber-dyeing dyes, the hair's natural melanin, for example, are typically decolored oxidatively using appropriate oxidants, such as hydrogen peroxide.

BACKGROUND

When hair is blonded—more particularly when hair is blonded at home by consumers themselves—the problem is that natural tints become completely covered, making multi-tone hair blonding difficult to realize.

In order to lend the hair a natural appearance, partially decolorizing both non-dyed and already dyed hair by the targeted application of oxidants is known from the prior art. The hair sections ("strands") to which the oxidant is applied typically bleach in portions, the result being a multi-tone hair color. Dyeing individual hair sections ("strands") with a different color is also known from the prior art. The oxidant, possibly comprising dye, is applied to the hair by means of a brush or similar tool, wherein the hair that is to remain untreated is protected against contact with the oxidant, possibly comprising dye, by means of solid, flat separating means, more particularly with soils from solid materials, such as aluminum, paper or Styrofoam and similar materials, or by means of a so-called "highlighting cap". Such a highlighting cap is disclosed in WO 2007/087978, for instance.

With the prior art highlighting method, the foils or the highlighting cap accumulate at the end of the method as solid waste, which must be discarded. This causes an environmental load. Handling the foils is difficult in part; for example, access to as yet untreated hair is obstructed by foils already in place. Moreover, foils made of paper, plastic and Styrofoam can adhere to the treated hair poorly and slip out.

Certain foil types and applications can involve overheating, because the possibility of dissipating the reaction heat of the exothermic oxidation process by evaporating volatile formula constituents, such as water for example, is severely restricted by the steam-impermeable foils.

Most foil types are not transparent. To be able to control the color development—especially towards the end of the specified application time—the foil must be at least partially handled, which can disrupt the color development process and, moreover, hinders the work sequence.

Blonding agents, particularly those that are supposed to achieve a strong lightening effect ("high lift"), typically contain a large quantity of ammonium hydroxide as the alkalizing agent. During the application time, usually at least from about 30 minutes to about 60 minutes, ammonia leaks out. In addition to the odor nuisance and mucous membrane irritation, this also reduces the effect of the agent during the lightening process. Moreover, blonding agents tend, particularly if not covered by highlighting foils and applied over large areas instead, to dry out during this relatively long application time, which also reduces the lightening effect. To compensate for the reduction in the lightening effect caused by drying out, a higher hydrogen peroxide concentration than is actually needed is typically selected for the oxidant. This can, in turn, lead to more severe structural damage to the keratin fibers and/or to a more severe irritation of the scalp than would actually be necessary.

Patent Applications EP2574331A2 and WO2014164213A1 disclose dyeing methods that permit multi-tone dyeing or blonding in one dyeing step, wherein a thickening agent, more particularly an anionic or cationic associative polymer (EP2574331A2) having a thickening effect is added to a hair blonding or bleaching agent in higher concentrations before application to selected hair sections or strands. The dye thickens on the hair strands to form a highly-viscous paste, thereby achieving a separating effect to adjacent hair sections or strands. The color exchange between adjacent strands, which were treated with various blonding or bleaching agents, is thus minimized. Over the total dye application time of approx. 30 to 60 minutes, the dye diffusion between adjacent strands, which are in physical contact with one another, cannot however be completely avoided. The corresponding commercial product for professional salon use is therefore marketed with the instruction that the color difference between adjacent strands should not be more than about 3 color tones. Otherwise, the color result would be impaired by a visible color exchange.

The present disclosure addressed the problem of preparing a method that permits multi-tone blonding in one process. The present disclosure also addressed the problem of preparing the most resource-efficient multi-tone blonding or lightening method possible, which involves no solid foil waste and uses, wherever possible, only materials from sustainable, non-fossil-based raw materials. In addressing this problem, it was particularly important for the foil substitutes to have a high separating force, just like the flat foils. In other words, permitting the cleanest possible separation of the various colored or bleached fiber sections or fiber strands, without any blonding agent exchange between the adjacent strands, which would result in broader stands being decolorized than actually intended. The present disclosure also addressed the problem of preparing a multi-tone blonding or lightening method that permits a simplified visual check of the decoloration development.

SUMMARY

Methods and kits for lightening keratinous fibers are provided. In an exemplary embodiment, a method for lightening keratinous fibers includes:
a) preparing a lightening composition (A), containing:
   a1) at least one alkalizing agent;
   a2) optionally at least one consistency enhancer; and
   a3) optionally at least one solvent, selected from water and at least one organic solvent; and
   a4) optionally at least one partially-oxidizing hair dye;
wherein when the lightening composition (A), relative to its weight, contains more than about 7 wt. % water, the lightening composition (A) has a pH value of from about 6.0 to about 11.5, measured at about 20° C., and wherein when the lightening composition (A), relative to its weight, contains from about 0 to about 7 wt. % water, a 30 wt. % dispersion of the lightening composition (A) in water has a pH value of from about 6.0 to about 12.0, measured at about 20° C.;
b) preparing an oxidant composition (B), containing:
  b1) from about 1 to about 18 wt. % hydrogen peroxide, relative to the weight of the composition (B); and
  b2) water;
wherein the oxidant composition (B) has a pH value of from about 2.5 to about 6.5, measured at about 20° C.;
c) preparing a polysaccharide composition (D), containing:
  c1) at least one polysaccharide adapted to form a gel with calcium ions in a hydrous medium and selected from alginic acid; iota carragheenan; pectin; at least one alkali metal salt of alginic acid, iota carragheenan, and pectin selected from ammonium salt, mono-, di- and trialkyl ammonium salt, mono-, di- and trialkanol ammonium salt, and magnesium salt; kappa carragheenan; and/or at least one alkali metal salt of kappa carragheenan selected from lithium salt and sodium salt;
  c2) from about 50 to about 99.9 wt. % water, relative to the weight of the polysaccharide composition (D);
  c3) optionally at least one alkalizing agent;
  c4) optionally at least one polymer, containing (meth) acrylic acid monomers, (meth)acrylic acid monomers, (meth)acrylamide monomers and/or 2-acrylamido-2-methylpropane sulfonic acid monomers;
  c5) optionally at least one oil in a total quantity of from about 0.1 to about 10 wt. % relative to the weight of the polysaccharide composition (D);
then
d) producing a mixture (M) of the lightening composition (A) and the oxidant composition (B), wherein the mixture (M) has a pH value of from about 6.0 to about 11, measured at about 20° C.;
e) applying at least one partial quantity of the mixture (M) on selected keratinous fibers;
f) applying the polysaccharide composition (D) to the selected keratinous fibers for a duration of from about 0.1 to about 60 minutes;
g) rinsing the keratinous fibers with water and, optionally, a cleaning agent; and
h) optionally post-treating the selected keratinous fibers with a conditioning agent and drying the selected keratinous fibers;
wherein the method includes applying at least one salt, not contained in the polysaccharide composition (D), of a polyvalent metal ion selected from calcium salt, strontium salt, barium salt and aluminum salt having a water solubility at 20° C. of at least about 500 mg/l, and, if c1) the polysaccharide comprises kappa carragheenan or one of the salts thereof, applying at least one salt, not contained in the polysaccharide composition (D), selected from potassium salt, calcium salt, strontium salt, barium salt and aluminum salt having a water solubility at 20° C. of at least about 500 mg/l.

In an exemplary embodiment, a kit for lightening keratinous fibers includes:
a polysaccharide composition (D), comprising:
  d1) at least one polysaccharide adapted to form a gel with calcium ions in a hydrous medium and selected from alginic acid; iota carragheenan; pectin; at least one alkali metal salt of alginic acid, iota carragheenan, and pectin selected from ammonium salt, mono-, di- and trialkyl ammonium salt, mono-, di- and trialkanol ammonium salt, and magnesium salt; kappa carragheenan; and/or at least one alkali metal salt of kappa carragheenan selected from lithium salt and sodium salt;
  d3) at least one alkalizing agent;
  d4) optionally at least one polymer containing (meth) acrylic acid monomers, (meth)acrylic acid ester monomers, (meth)acrylamide- and/or 2-acrylamido-2-methylpropansulfonic acid monomers, wherein the at least one polymer is unsubstituted or is substituted with ethoxylated, C6-C24-alkyl- or C6-C24-alkenyl groups
a gel composition (C") comprising:
  c1) at least one salt of a polyvalent metal ion, selected from calcium salt, strontium salt, barium salt and aluminum salt having a water solubility at 20° C. of at least about 500 mg/l, and, if d1) the polysaccharide comprises kappa carragheenan or one of the salts thereof, at least one salt, selected from potassium, calcium salt, strontium salt, barium salt and aluminums salt having a water solubility at 20° C. of at least about 500 mg/l; and
  d3) optionally at least one cation polymer;
wherein the gel composition (C) has a pH value of from about 4 to about 12, measured at 20° C.;
  optionally a lightening composition (A), comprising:
    a1) at least one alkalizing agent;
    a2) optionally at least one consistency enhancer;
    a3) optionally at least one solvent, selected from water, one or more mono- or polyvalent alcohols having from about 2 to about 9 carbon atoms, and mixtures thereof; and
    a4) optionally at least one partially-oxidizing hair dye;
  wherein when the lightening composition (A), relative to its weight, contains more than about 7 wt. % water, the lightening composition (A) has a pH value of from about 6.0 to about 11.5, measured at about 20° C., and
  wherein when the lightening composition (A), relative to its weight, contains from about 0 to about 7 wt. % water, a 30 wt. % dispersion of the lightening composition (A) in water has a pH value of from about 6.0 to about 12.0, measured at about 20° C.; and
  optionally an oxidant composition (B), comprising:
    b1) from about 1 to about 18 wt. % hydrogen peroxide, relative to the weight of the composition (B); and
    b2) water;
  wherein the oxidant composition (B) has a pH value of from about 2.5 to about 6.5, measured at about 20° C.;
  wherein the components (D), (C), (A), if present, and (B), if present, are are physically separated from one another.

In another embodiment, a method for lightening keratinous fibers includes coating the keratinous fiber strands with at least one polysaccharide salt, selected from calcium alginate, potassium kappa carragheenat, calcium kappa carragheenat, calcium iota carragheenat, calcium pectinate, aluminum alginate, aluminum kappa carragheenat, aluminum iota carragheenat, aluminum pectinate, strontium alginate, strontium kappa carragheenat, strontium iota carragheenat, strontium pectinate, barium alginate, barium kappa carragheenat, barium iota carragheenat, barium pectinate, and/or mixtures thereof; and lightening the coated keratinous fibers.

DETAILED DESCRIPTION

The present disclosure also addressed the problem of preparing a method for the oxidative lightening or blonding of keratin fibers, wherein the unwanted drying of the lightening agent or dye is reduced to permit the use of lower concentrations of hydrogen peroxide while achieving a uniform lightening effect. The present disclosure also addressed the problem of preparing a method for the oxidative lightening or blonding of keratin fibers with reduced scalp irritation potential. The present disclosure also addressed the problem of preparing a method for the oxidative lightening or blonding of keratin fibers, which reduces the unwanted release of ammonia during the application time on the keratin fibers.

In principle, the method as contemplated herein is also suitable for achieving a monotone color change, more particularly for the lightening and/or blonding of keratin fibers. The entire keratin fiber ensemble, e.g. all the main hair, can be treated with the blonding or lightening composition uniformly or in sections, e.g. strand-like, variation of the color tones and highlights, and then subjected to the film-formation procedure as contemplated herein.

The subject matter of the present disclosure is a method for lightening or blonding keratinous fibers, said method having a reduced release of ammonia, thereby permitting, with lower concentrations of hydrogen peroxide, a uniform lightening effect, said method also allowing the hair to be blonded in a single treatment session and, at the same time, creating a multi-tone dyeing effect with various sections (strands), more particularly lighter ("highlights") sections (strands), wherein the use of solid, flat separating aids, more particularly foils from solid materials such as aluminum, paper or Styrofoam and similar materials is not required.

To achieve this purpose, the ready-to-use blonding or lightening agent, which typically has a stronger alkali pH value, or its individual components, is first mixed with at least one selected salt of a polyvalent metal ion, selected from calcium-, strontium-, barium- and aluminum salts and, under certain preconditions, selected from potassium salts, in each case with a water solubility at about 20° C. of at least about 500 mg/l, wherein the polyvalent metal ions form a gel or a gelled film with certain polysaccharides in a hydrous medium.

Instead of mixing the ready-to-use blonding or lightening agent or its individual components with said selected salt of a polyvalent metal ion, the ready-to-use blonding or lightening agent can also first be applied to selected keratin fiber sections, more particularly hair sections, or keratin fiber strands, more particularly hair strands, in the usual way and then sprayed or coated with a hydrous solution of said selected salt or a polyvalent metal ion. The fiber sections or strands treated with said selected salt can then be sprayed or coated with a hydrous solution of a selected polysaccharide, which interacts with said selected cations and solidifies into to a film-forming gel. This film acts, similar to the strand foils of the known method, like a separating layer, which allows adjacent fiber sections or strands to be dyed or bleached different colors. Moreover, this film acts like a transparent barrier that slows the release of ammonia and the evaporation of water, and also permits a simple visual check of the blonding or lightening effect during the application time.

To the extent required by the invention, the expressions "keratinous fibers" and "keratin fibers" are human air, but can also include fur, wool and feathers. To the extent required by the invention, "then" means preferably a period from about 1 to about 600 seconds.

The subject matter of the present disclosure is a method for lightening and/or blonding keratinous fibers, characterized by the following method steps I. preparing a blonding or lightening composition (A), comprising a)i. at least one alkalizing agent,
a)ii. optionally at least one consistency enhancer and
a)iii. optionally at least one solvent, selected from water and at least one organic solvent, preferably selected from one or more monovalent or polyvalent alcohols having from about 2 to about 9 carbon atoms, polyethylene glycols having from about 2 to about 20 ethylene glycol units, as well as mixtures of said solvents, and
a)iv. optionally at least one partially-oxidizing hair dye,
a)v. wherein the blonding or lightening composition (A), insofar as, relative to its weight, it comprises more than about 7 wt. % water, has a pH value in the range of from about 6.0 to about 11.5, measured at about 20° C. and, insofar as the composition (A), relative to its weight, comprises from about 0 to about 7 wt. % water, its 30 wt. % dispersion in water has a pH value in the range of from about 6.0 to about 12.0, preferably from about 7.5 to about 11.5, more preferably from about 8 to about 11.0, in each case measured at about 20° C.;

II. preparation of an oxidant composition (B), comprising
b)i. from about 1 to about 18 wt. % hydrogen peroxide, relative to the weight of the composition (B), and
b)ii. water,
b)iii. wherein the oxidant composition (B) has a pH value in the range from about 2.5 to about 6.5, preferably in the range from about 3 to about 5.5, more particularly in the range from about 3.5 to about 5.0, in each case measured at about 20° C.;

c. preparation of a polysaccharide composition (D), comprising
c)i. at least one polysaccharide, which can form a gel with calcium ions in hydrous medium and which is selected from alginic acid, kappa carragheenan, iota carragheenan and pectin, and/or at least one salt of the aforementioned polysaccharide, selected from the alkali metal-, ammonium-, mono-, di- and trialkyl ammonium-, mono-, di- and trialkanol ammonium- and magnesium salts, preferably in a total quantity of from about 0.1 to about 5 wt. %, preferably from about 0.5 to about 2 wt. %, more preferably from about 0.5 to about 2.5 wt. %, in each case relative to the weight of the composition (D), wherein in the case of the kappa carragheenan, the alkali metal salt is selected only from lithium- and sodium salts,
c)ii. from about 50 to about 99.9, preferably from about 60 to about 95, more preferably from about 80 to about 90 wt. % water, in each case relative to the weight of the composition (D),
c)iii. optionally at least one alkalizing agent, which is preferably selected from powdery sodium silicates, more particularly sodium meta silicates,
c)iv. optionally at least one polymer, comprising (meth) acrylic acid-, (meth)acrylic acid-, (meth)acrylamide- and/or 2-acrylamido-2-methylpropane sulfonic acid monomers, preferably in a total quantity of from about 0.05 to about 3 wt. %, preferably from about 0.2 to about 0.5 wt. %, relative to the weight of the composition (D),
c)v. optionally at least one oil in a total quantity of from about 0.1 to about 10 wt. %, preferably from about 0.3 to about 5 wt. %, more preferably from about 1 to about 3 wt. %, in each case relative to the weight of the polysaccharide composition (D), wherein optionally the polysaccharide composition (D) is produced by mixing a solid, preferably powdery, polysaccharide composition (D'), comprising c)i and optionally c)iii and/or optionally c)iv, with the component c)ii and optionally with the component c)v in situ or from about 0.01 to about 24 hours before applying the color-changing method as contemplated herein, then, preferably from about 1 to about 600 seconds thereafter, d. producing a mixture (M) of (A) and (B), having a pH value in the range of from about 6.0 to about 11, in each case measured at about 20° C.; after from about 1 to about 600 seconds e. applying at least one partial quantity of (M) on at least one keratin fiber section to be blonded and/or lightened, or applying the agent (M) to the entire keratin fiber ensemble to be treated; from about 1 to about 600 second, preferably from about 5 to about 300 seconds, more preferably from about 5 to about 60 seconds thereafter f. applying, preferably spraying, the polysaccharide composition (D) to the keratin fiber section(s) treated with (M) or the keratin fiber ensemble treated with (M);

g. repeating steps e. and f. as many times as desired, h. leaving on the keratinous fibers for a time of from about 0.1 to about 60 minutes, preferably from about 1 to about 50 minutes, more preferably from about 10 to about 45 minutes, most preferably from about 30 to about 45 minutes, and then rinsing the keratinous fibers with water and, if required, with a cleaning agent, post-treating the fibers with a conditioning agent and then drying, if required, wherein the method comprises the application of at least one salt of a polyvalent metal ion, selected from calcium-, strontium-, barium- and aluminum salts having a water solubility at about 20° C. of at least about 500 mg/l, and also in case the polysaccharide which forms a gel with calcium ions comprises kappa carragheenan or one of the salts thereof, the method comprises the application of at least one salt, selected from potassium-, calcium-, strontium-, barium- and aluminum salts having a water solubility at from about 20° C. of at least about 500 mg/l, wherein these salts are not included in the polysaccharide composition (D).

The present disclosure relates to the oxidative color change, more particularly the lightening and/or blonding of keratinous fibers, more particularly of hair. Because when keratinous fibers, more particularly hair, is treated with oxidants, more particularly with hydrogen peroxide, the fiber's natural color/melanin is destroyed to a certain extent, the fibers/hair is inevitably lightened, the color of such fibers/hair changes, even without the presence of oxygen. To the extent required by the present disclosure, therefore, the expression "color change" also comprises lightening and dyeing with one or more dyes.

A person skilled in the art knows various methods for changing the color of human hair. Generally, human hair is dyed using partially-oxidizing dyes or oxidizing dyes, which are produced by oxidatively coupling one or more developer components among one other, or with one or more coupler components. Coupler and developer components are also referred to as oxidizing dye precursors. The dyes achieved with oxidative dyes are typically referred to as permanent or semi-permanent dyes. As oxidants, these agents usually contain hydrogen peroxide. Because hydrogen peroxide has inadequate storage stability in the alkaline pH range, oxidative dyes typically comprise two components, which are mixed together immediately, i.e. within a period of from about 1 to about 600 seconds, prior to use. The first component, referred to below as "oxidant composition (B)", comprises hydrogen in a hydrous solution or emulsion, wherein this composition has an acidic pH value in the range of from about 2.5 to about 6.5, preferably in the range of from about 3 to about 5.5, more preferably in the range of from about 3.5 to about 5.0, in each case measured at about 20° C., in order to stabilize the hydrogen peroxide.

The second component, referred to below as "blonding or lightening composition (A)" comprises one or more alkalizing agents in a quantity in which the application mixture of the two components has a pH value in the range of from about 8 to about 11, in each case measured at about 20° C. The blonding or lightening agents (A) used as contemplated herein contain no oxidizing dye precursors and only relatively small quantities of partially-oxidizing dyes. The latter serve to cover unwanted color shades that can occur during melanin oxidation. In addition, there are also blonding kits and blonding methods wherein the application mixture of the two components has a pH value in the range of approx. 6 to 7.9; the lightening results of such so-called "acidic" blonding, however, do not achieve the quality achieved with stronger alkaline application mixtures. For the blonding or lightening result, it is important for the ready-to-use blonding or lightening agent, which is obtained by mixing blonding or lightening composition (A) with composition (B), to have a pH value in the range of from about 6.5 to about 11.0, preferably from about 8 to about 10.5, more preferably from about 8.5 to about 9.5, in each case measured at about 20° C. At such pH values, the outer keratin fiber layer opens to the optimal extent to absorb the oxidant, and the oxidative effect of the hydrogen peroxide and possibly other peroxide compounds develops to the optimal extent.

Gel-Forming Salt

An essential part of the dyeing method(s) preferred as contemplated herein is at least one salt of a polyvalent metal ion, selected from calcium-, strontium, barium- and aluminum salts having a water solubility at about 20° C. of at least about 500 mg/l and, under certain conditions, also potassium salts having a water solubility at about 20° C. of at least about 500 mg/l which, once mixture (M) from blonding- or lightening composition (A) and oxidant composition (B) has been applied to the keratin fibers, is brought into contact with at least one polysaccharide, which can form a gel with calcium ions. As a result, a film-like gel forms on mixture (M), which protects said mixture from drying out, reduces the release of ammonia and acts as highlighting foils if desired.

Said polysaccharide, which can form a gel with calcium ions, is preferably selected from alginic acid, kappa carragheenan, iota carragheenan and pectin, and/or at least one salt of the aforementioned polysaccharides, selected in turn from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts.

At about 20° C., the at least one salt d)i has a water solubility of at least about 500 mg/l, preferably of at least about 40 g/l, more preferably of at least about 200 g/l, and most preferably of at least about 350 g/l. The preferred calcium chloride as contemplated herein has a water solubility of about 740 g/l at about 20° C. Other most preferred salts d)i as contemplated herein are selected from calcium acetate (water solubility about 374 g/l), calcium lactate, calcium gluconate, calcium gluconate lactate. Aluminum chloride, aluminum hydroxychloride, aluminum sulfate, aluminum lactate, aluminum acetate, aluminum gluconate are likewise preferred. Potassium chloride, potassium acetate, potassium lactate, potassium gluconate and potassium sulfate are preferred for the gelling of kappa carragheenan, potassium, chloride, potassium lactate, and potassium gluconate being most preferred. Strontium chloride and barium chloride are also suitable. Preferably, mixtures of the aforementioned salts can also be contained.

Polysaccharide, selected from alginic acid, kappa carragheenan, iota carragheenan and pectin, and/or at least one salt of said polysaccharides A further essential component of the lightening and blonding methods preferred as contemplated herein is at least one polysaccharide, which forms a gel with calcium ions in hydrous medium. Polysaccharides preferred as contemplated herein, which can form a gel with calcium ions in a hydrous medium, are preferably selected from alginic acid, kappa carragheenan, iota carragheenan and pectin, as well as at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts. Hydrous solutions of said polysaccharides and polysaccharide salts demonstrate, depending on concentration, only a slightly increased viscosity, but do not yet form a solid gel.

Alginic acid, sodium alginate, ammonium alginate, magnesium alginate, monoethanolammonium alginate, kappa carragheenan, the lithium salt of kappa carragheenan, the sodium salt of kappa carragheenan, iota carragheenan, the lithium salt of iota carragheenan, the sodium salt of iota carragheenan, the potassium salt of iota carragheenan, the ammonium salt of iota carragheenan, pectin, sodium pectinate, ammonium pectinate, potassium pectinate, as well as mixtures of such substances, are most preferred. Most preferred mixtures as contemplated herein are those from alginic acid and sodium alginate, more particularly mixtures from alginic acid and sodium alginate in the weight ratio of alginic acid to sodium alginate in the range of from about 1:2 to about 2:1, preferably in the range from about 0.8 to about 1.25, most preferably in the weight ratio of about 1:1.

The aforementioned polysaccharides and/or the mentioned salts demonstrate a thickening behavior that is largely independent of pH. However, they gel in contact with certain polyvalent ions such as calcium, strontium-, barium- and aluminum ions. Moreover, kappa carragheenan also gels in contact with potassium ions.

To the extent required by the present disclosure, this behavior is used to produce a foil-like film on selected keratin fiber sections or keratin fiber strands once the blonding or lightening agent has been applied, wherein said film reduces the drying of the composition during the application time and the release of ammonia, and also prevents, or at least drastically reduces, the exchange with the blonding or lightening agent applied to the adjacent strands. Three embodiments of the method as contemplated herein produce said film.

In the first preferred embodiment of the method as contemplated herein, at least one of the aforementioned salts of a polyvalent metal ion, selected from calcium-, strontium-, barium- and aluminum salts having a water solubility at about 20° C. of at least about 500 mg/l and, under certain conditions, also selected from potassium salts having a water solubility at about 20° C. of at least about 500 mg/l, is included in a composition (A) or (B) or in both compositions (A) and (B) and/or is added to the ready-to-use blonding or lightening mixture of (A) and (B) via a third component). If the keratin fiber strands are adequately treated with salt-comprising blonding or lightening agents, a polysaccharide composition (D) comprising at least one polysaccharide, which can form a gel with calcium ions in a hydrous medium, is applied. Polysaccharides preferred as contemplated herein, which can form a gel with calcium ions in a hydrous medium, are preferably selected from alginic acid, kappa carragheenan, iota carragheenan and pectin, as well as at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts. The polysaccharide composition (D) can, for example, be applied, or also sprayed, to the keratin fibers by means of a brush or similar applicator. As a result of the precipitation reaction between the polysaccharide or the soluble salt thereof and the gel-forming cat ions from one of compositions (A) or (B), a film-like gel, which acts like a separating layer similar to a highlighting foil, forms in-situ n the keratin fibers treated with the blonding or lightening agent.

In a second, most preferred embodiment of the method as contemplated herein, a least one of the aforementioned salts of a polyvalent metal ion, selected from calcium-, strontium-, barium- and aluminum salts having a water solubility at about 20° C. of at least about 500 mg/l and, under certain conditions, also selected from potassium salts having a water solubility at about 20° C. of at least about 500 mg/l, exists in powder form and is added to the blonding or lightening composition (A) which, as explained below, preferably constitutes a powdery blonding or lightening composition (A-2), before this is mixed with oxidation mixture (B) for the blonding or lightening agent (M). The mixture is then applied to the keratin fiber strands. The polysaccharide composition (D) is then applied. This can be achieved by means of a brush or similar applicator, preferably however by being sprayed onto the keratin fibers.

In a third specific embodiment of the method as contemplated herein, a least one of the aforementioned polyscaccharides and/or at least of the aforementioned salts of a polyvalent metal ion, selected from calcium-, strontium-, barium- and aluminum salts having a water solubility at about 20° C. of at least about 500 mg/l and, under certain conditions, also selected from potassium salts having a water solubility at about 20° C. of at least about 500 mg/l, exists in the form of a hydrous solutions as a gelling composition (C) and, similar to the polysaccharide composition (D) explained above, is applied to the keratin fiber strands, which are adequately treated with blonding or lightening agents. This can likewise be achieved by means of a brush or similar applicator, preferably however by being sprayed onto the keratin fibers. The hydrous preparation of the polysaccharide, which can gel with calcium ions, is preferably applied first. The gelling composition (C) is then applied.

For the three aforementioned embodiments of the lightening or blonding agents preferred as contemplated herein, the weight ratio of polysaccharide composition (D) to mixture (M) of blonding or lightening composition (A) and oxidation composition (B) is preferably in the range of from about 1:20 to about 1:2, most preferably in the range of from about 1:10 to about 1:5.

For the third of the aforementioned lightening or blonding methods preferred as contemplated herein, it is also most preferable for the weight ratio of polysaccharide composition (D) to gelling composition (C) to be in the range of from about 0.2:1 to about 2:1, preferably in the range of from about 0.5:1 to about 1.5:1 and is most preferably about 1.1.

For the third of the three aforementioned preferred embodiments of the lightening or blonding agents preferred as contemplated herein, the weight ratio of gelling composition (D) to mixture (M) of blonding or lightening composition (A) and oxidation composition (B) is likewise preferably in the range of from about 1:20 to about 1:2, most preferably in the range of from about 1:10 to about 1:5.

If the blonding or lightening reaction has finished when the recommended application time has lapsed, all of the hair treatment agent can be washed out with water and optionally a shampoo in one single step. The time-consuming processing, as required with the known highlighting foils, is not needed in this case. Since the polysaccharides used as contemplated herein constitute naturally-occurring biopolymers, they are readily bio-degradable in sewage plants. Therefore, they are easier to dispose of than sheet-like foil materials.

Blonding or lightening composition (A)

The blonding or lightening composition (A) can be solid, more particularly powdery, but also liquid (from about 0 to about 500 mPas at about 20° C.), medium-viscosity (> from about 400 to about 4000 mPas at about 20° C.), creamy (> from about 4000 to about 40,000 mPas at about 20° C.) or pasty (> from about 40,000 to about 4,000,000 mPas at about 20° C.).

Solid blonding or lightening compositions (A) can also exist in tablet or granulated form.

Lightening Compositions (A-1) and (A-2)

In a first preferred embodiment of the invention, composition (A) is an agent which, after being mixed with a hydrogen peroxide-comprising hydrous composition (B), serves to lighten and/or blond keratin fibers, more particularly human hair.

In a first most preferred embodiment of the invention, the lightening composition (A-1) is liquid (from about 0 to about 500 mPas at about 20° C.), medium-viscosity (> from about 400 to about 4000 mPas at about 20° C.) or creamy (> from about 4000 to about 40,000 mPas at about 20° C.) and comprises water in a quantity of more than from about 7 wt. % to about 90 wt. %, preferably from about 20 to about 85 wt. %, more preferably from about 40 to about 75 wt. %, in each case relative to the weight of the lightening composition (A-1).

In a second most preferred embodiment of the invention, the lightening composition (A-2) is solid, more particularly powdery, but can also exist in tablet or granulated form, and comprises from about 0 to less than about 7 wt. % water, relative to the weight of the respective lightening composition (A-2).

pH value of the blonding or lightening compositions (A-1)

The blonding or lightening compositions (A-1) have a pH value in the range from about 6.5 to about 12.0, preferably from about 8 to about 11.5, more preferably from about 8.5 to about 11.0, in each case measured at about 20° C.

The blonding or lightening agents (A-2) are solid, preferably powdery, or pasty and contain no or only up to approx. 7 wt. % water. In addition, they contain a quantity of alkalizing agent such that their about 30 wt. % dispersion in water has a pH value in the range of from about 6.0 to about 12.0, preferably from about 7.5 to about 11.5, most preferably from about 8 to about 11.0, in each case measured at about 20° C.

Alkalizing Agent

The blonding or lightening agents (A), namely (A-1) and (A-2) contain at least one alkalizing agent, selected from ammonium hydroxide, monoethanolamine and sodium silicates, as well as mixtures thereof.

Preferably, the lightening composition (A-1) comprises ammonium hydroxide, i.e. ammonia in the form of its hydrous solution. The corresponding hydrous ammonia solutions can be from about 10 to about 35% solutions (calculated in wt. % of about 100 g hydrous ammonia solution correspondingly comprising from about 10 to about 35 g of ammonia). Ammonia in the form of about 20 to about 30 wt. % solution is preferably used, most preferably in the form of about 25 wt. % solution.

In a most preferred embodiment, the compositions (A-1) used as contemplated herein are wherein they contain ammonium hydroxide in a quantity from about 0.20 to about 18.0 wt. %, preferably from about 1.0 to about 1.5 wt. %, more preferably from about 2.0 to about 12.0 wt. % and most preferably from about 3.0 to about 9 wt. %—relative to the weight of the composition (A) used as contemplated herein.

In addition to and/or instead of ammonium hydroxide, compositions (A) preferably used as contemplated herein, more particularly the compositions (A-1) used as contemplated herein, contain monoethanolamine.

In order to achieve maximum odor minimization and optimize the authenticity properties, monoethanolamine in a total quantity of from about 0.2 to about 9.0 wt. %, preferably from about 1.0 to about 7 wt. %, more preferably from about 2.0 to about 6.0 wt. % and most preferably from about 3.0 to about 5.5 wt. %, relative to the weight of the composition (A) as contemplated herein.

In order to achieve maximum odor minimization and optimize the authenticity properties, the compositions (A-1) as contemplated herein contain monoethanolamine in a total quantity of from about 0.2 to about 9.0 wt. %, preferably from about 1.0 to about 7 wt. %, more preferably from about 2.0 to about 6.0 wt. % and most preferably from about 3.0 to about 5.5 wt. %, relative to the weight of the compositions (A-1) as contemplated herein.

Sodium silicates according to the present disclosure are chemical compounds, which are composed of sodium oxide and silicon dioxide, and which can occur in various molar ratios (monosilicate, metasilicate and polysilicate). One example of a sodium silicate, is the sodium salt of ortho silica having the molecular formula Na4SiO4, which is also referred to as sodium ortho silicate.

Other examples of suitable sodium silicates are di-sodium silicate and/or sodium meta silicate having the molecular formula Na2SiO3, di-sodium silicate having the molecular formula Na2Si2O5 or the di-sodium silicate having the molecular formula Na2Si3O7.

Silicates in amorphic form can be produced by melting together silicon dioxide and alkali dioxide in molar ratios of from about 1:1 and about 4:1. The solids thus obtained are dissolved at around about 150° C. and about 5 bar vapor pressure, in order to obtain a solution of the sodium silicates in water; these corresponding solutions are alkali soluble glasses Solidified, glass-like (amorphous) sodium silicates or the hydrous solutions thereof are referred to as alkali silicates. These are also referred to as sodium silicates. Within this invention, sodium soluble glasses are covered by the definition of sodium silicates.

The molar composition with soluble glasses is usually from about 2 to about 4 mol SiO2 on about 1 mol alkali oxide (Na2O).

One example of a preferred sodium silicate is sodium soluble glass, which exists in the form of its hydrous solution, has a Na2O content of from about 7.5 to about 8.8 wt. % and at least a SiO2 content of from about 25.0 to about 28.5 wt. % and the CAS No. 1344-09-5 (Chemical Abstracts Number).

Other compositions (A) preferred as contemplated herein contain, as the alkalizing agent, at least one sodium silicate, preferably sodium meta silicate or sodium soluble glass, in a total quantity of from about 0.1 to about 25 wt. %, preferably from about 0.5 to about 20 wt. %, more preferably from about 1 to about 17 wt. %, most preferably from about 2 to about 9 wt. %, in each case relative to the weight of the composition (A) used as contemplated herein.

The use of sodium silicate as the alkalizing agent is most preferred for the compositions (A-2) used as contemplated herein.

Other compositions (A2) preferred as contemplated herein contain, as the alkalizing agent, at least one sodium silicate, preferably sodium meta silicate or sodium soluble glass, in a total quantity of from about 0.1 to about 25 wt. %, preferably from about 0.5 to about 20 wt. %, more preferably from about 1 to about 17 wt. %, most preferably from about 2 to about 9 wt. %, in each case relative to the weight of the composition (A2) used as contemplated herein.

Other compositions (A) used as contemplated herein, more particularly the compositions (A-2), contain as the alkalizing agent at least one alkali metal or earth alkali metal carbonate, preferably selected from sodium carbonate, potassium carbonate and magnesium carbonate, as well as mixtures of said carbonates. The at least one alkali metal or earth alkali metal carbonate is preferably included in a total quantity of from about 0.1 to about 25 wt. %, preferably from about 0.5 to about 20 wt. %, more preferably from about 1 to about 10 wt. %, in each case relative to the weight of the composition (A) as contemplated herein. The at least one alkali metal or earth alkali metal carbonate is preferably included in a total quantity of from about 0.1 to about 25 wt. %, preferably from about 0.5 to about 20 wt. %, more preferably from about 1 to about 10 wt. %, in each case relative to the weight of the composition (A-2) as contemplated herein.

Other alkalizing agents, such as potassium hydroxide (KOH) and sodium hydroxide (NaOH) can also be contained, typically in a total quantity of from about 0.05 to about 1.5 Wt. %, preferably from about 0.1 to about 0.6 wt. %, relative to the weight of the composition (A) used as contemplated herein.

Basic amino acids, more particularly Arginin, Lysin or Histidin, as well as the mixtures of said amino acids, more particularly mixtures of Arginin and Lysin can also be included in preferred compositions (A) as alkalizing agents, preferably in a total quantity of from about 0.01 to about 10 wt. %, more preferably from about 0.1 to about 5 wt. %, most preferably from about 0.5 to about 3 wt. %, in each case relative to the weight of the composition as contemplated herein (A). Compositions (A) most preferred as contemplated herein contain mixtures of the aforementioned alkalizing agents, more particularly ammonium hydroxide/sodium silicate/potassium hydroxide mixtures, ammonium hydroxide/monoethanolamine/sodium silicate/potassium hydroxide mixtures, monoethanolamine/sodium silicate/potassium hydroxide mixtures, ammonium hydroxide/sodium silicate/potassium hydroxide/arginine mixtures, ammonium hydroxide/monoethanolamine/sodium silicate/potassium hydroxide/arginine mixtures, monoethanolamine/sodium silicate/potassium hydroxide/arginine mixtures, sodium silicate/magnesium carbonate mixtures and sodium meta silicate/magnesium carbonate mixtures.

Consistency Enhancers

Compositions (A-1) used as contemplated herein, more particularly the compositions
(A-1), contain at least one consistency enhancer. Suitable consistency enhancers are particularly fat substances having a melting point of from about 25° C. or over at about 1013 mbar ambient pressure, as well as polymer thickeners, which are different to the polysaccharides, which form a gel with calcium ions in hydrous medium, used as contemplated herein. Such consistency enhancers are preferably selected from linear saturated 1 alkanols having from about 12 to about 30 hydrogen atoms and glyceryl fatty acid esters of general Formula (I),

wherein
R1, R2 and R3 denote, independently of one another, a hydrogen atom or a grouping independent of each other or a grouping of Formula (II),

wherein
R4 denotes an unbranched or branched, saturated or unsaturated C11-C27-alkyl group, on condition that at least one and a maximum of two of the radicals are selected from R1, R3R2 and R3 denotes a grouping of Formula (II).

The radical R4 in Formula (II) denotes an unbranched or branched, saturated or unsaturated C11-C27-alkyl group.

R4 preferably denotes an unbranched, saturated C11-C27-alkyl group. R4 also preferably denotes an unbranched, saturated C13-C23-alkyl group. R4 most preferably denotes an unbranched, saturated C15-C17-alkyl group.

Glyceryl fatty acid esters of general Formula (I) most preferred as contemplated herein are selected from at least one compound from the group of Formulas (Ia) to (Id):

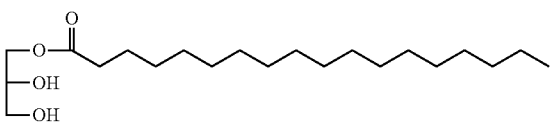

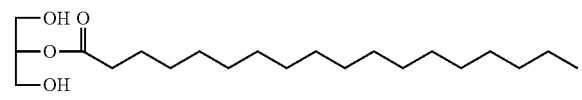

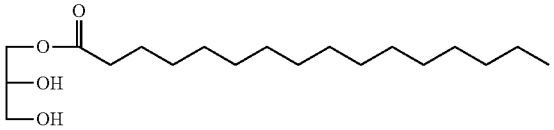

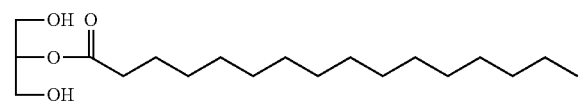

The compounds of Formulas (Ia) to (Id) are also known as glyceryl monostearate and glyceryl monopalmitate.

Other blonding or lightening compositions (A) as contemplated herein are wherein at least one compound from the group of Formulas (Ie) to (Ih) is included as glyceryl fatty acids:

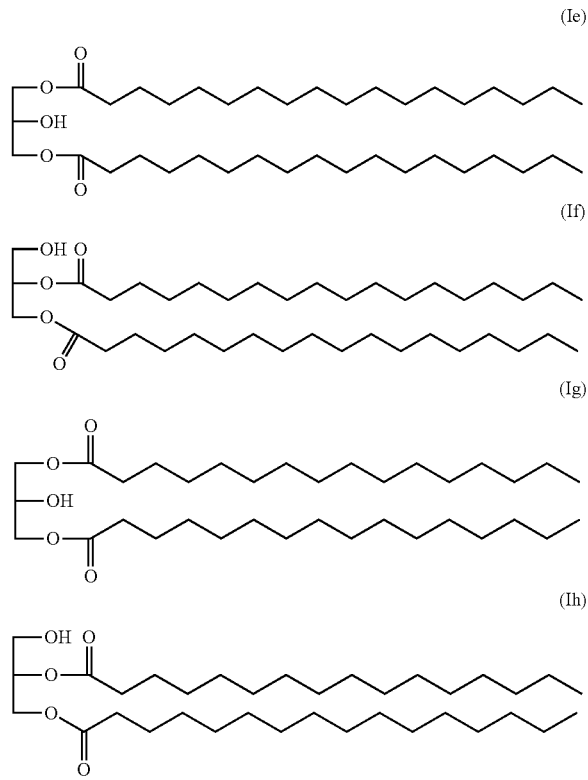

The compounds of Formulas (Ie) to (Ih) are also known as glyceryl distearate and glyceryl dipalmitate.

Linear saturated 1-alkanols having from about 12 to about 30 carbon atoms are selected from lauryl alcohol, myristyl alcohol, cetyl alcohol, stearyl alcohol, arachidyl alcohol and behenyl alcohol, as well as from mixtures of said alcohols, most preferably from cetyl alcohol, stearyl alcohol, arachidyl alcohol, behenyl alcohol and cetyl alcohol/stearyl alcohol mixtures.

Other consistency enhancers preferred as contemplated herein are ethylenglycolmonosterate, ethylenglycoldistearate, waxes, glycerintriester, which have a boiling point of about 25° C. or over, more particularly hydrated castor oil (castor wax) and ethoxylated, hydrated castor oils, and fatty acid-fatty alcohol esters having a boiling point of about 25° C. or over, as well as mixtures of said substances.

Compositions (A), more particularly compositions (A-1), preferred as contemplated herein contain at least one fatty substance consistency enhancer in a total quantity of from about 0.1 to about 30 wt. %, preferably from about 0.5 to about 20 wt. %, more preferably from about 2 to about 15 wt. %, most preferably from about 3 to about 10 wt. %, in each case relative to the weight of the composition (A). Other compositions (A), more particularly compositions (A 1), preferred as contemplated herein contain at least one linear saturated 1-alkanol having from about 12 to about 30 hydrogen atoms in a total quantity of from about 0.1 to about 30 wt. %, preferably from about 0.5 to about 20 wt. %, more preferably from about 2 to about 15 wt. %, most preferably from about 3 to about 10 wt. %, in each case relative to the weight of the composition (A).

In a more preferred embodiment of the invention, the compositions (A), (B), (C) as contemplated herein are free of anionic or cationic associative polymers, which are substituted with possibly ethoxylated, C6-C24-alkyl- or C6-C24-alkenyl groups. In a most preferred embodiment of the invention, the compositions (A), (B) (C) and (D) used as contemplated herein are free of anionic or cationic associative polymers, which are substituted with possibly ethoxylated C6-C24-Alkyl- or C6-C24-alkenyl groups and selected from acrylates/Ceteth-20 Itaconate copolymers, Polyurethane-39-polymers, acrylates/Beheneth-25 methacrylate copolymers and acrylates/C10-30 alkyl acrylate cross polymers.

Gelling metal salt in composition (A)

In so far as the at least one salt of a polyvalent metal ion, selected from calcium, calcium-, strontium, barium and aluminum salts having a water solubility at about 20° C. of at least about 500 mg/l and, under certain conditions, from potassium salts having a water solubility at about 20° C. of at least about 500 mg/l, is included in the blonding or lightening composition (A), preferably in a total quantity of from about 0.1 to about 5 wt. %, more preferably from about 0.2 to about 3 wt. %, most preferably from about 0.5 to about 2.5 wt. %, in each case relative to the weight of composition (A). Most preferably, the blonding or lightening agent (A) comprises at least one salt d) which, at about 20° C., has a water solubility of at least about 500 mg/l, preferably of at least about 40 g/l, more preferably of at least about 200 g/l, and most preferably of at least about 350 g/l. The preferred calcium chloride as contemplated herein has a water solubility of about 740 g/l at about 20° C. Other most preferred salts d)i as contemplated herein are selected from calcium acetate (water solubility of about 374 g/l), calcium lactate, calcium gluconate, calcium gluconate lactate. Aluminum chloride, aluminum hydroxychloride, aluminum sulfate, aluminum lactate, aluminum acetate, aluminum gluconate are likewise preferred. Potassium chloride, potassium acetate, potassium lactate, potassium gluconate and potassium sulfate are preferred for the gelling of kappa carragheenan, potassium, chloride, potassium lactate, and potassium gluconate being most preferred. Strontium chloride and barium chloride are also suitable. Preferably, mixtures of the aforementioned salts can also be contained. Most preferably, the blonding or lightening composition (A) comprises at least one salt, selected from calcium chloride, calcium actate, calcium gluconate and calcium gluconatlactate, as well as mixtures thereof in a total quantity of from about 0.1 to about 5 wt. %, more preferably from about 0.2 to about 3 wt.-%, most preferably from about 0.5 to about 2.5 wt. %, in each case relative to the weight of the composition (A). Most preferably, the blonding or lightening composition (A) comprises from about 0.1 to about 5 wt. %, more preferably from about 0.2 to about 3 wt. %, most preferably from about 0.5 to about 2.5 wt. %, calcium chloride, in each case relative to the weight of the composition (A).

Partially-Oxidizing Dyes

In a further preferred embodiment, the compositions (A) as contemplated herein contain at least one partially-oxidizing dye. Partially-oxidizing dyes can be sub-divided into anionic, cationic and non-ionic partially-oxidizing dyes. The partially-oxidizing dyes are preferably selected from the nitrophenylenediamines, the nitroaminophenols, the azo dyes, the anthraquinones, the triarylmethane dyes or the indophenols and the physiologically acceptable salts thereof. Preferably, at least one partially-oxidizing dye is included in a total quantity of from about 0.001 to about 3 wt. %, relative to the weight of the composition (A) as contemplated herein. In oxidizing blonding agents (A-1) and (A-2), partially-oxidizing dyes serve to equalize unwanted red and orange tones, which can be produced when the hair's own melanin decomposes.

Preferred anionic partially-oxidizing dyes are the compounds known under the international designations and/or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromphenol blue and tetrabromphenol blue. Tetrabromphenol blue, Acid Red 33 and Acid Red 52, as well as the mixtures thereof are most preferred for blonding agents (A-1) and (A-2) as contemplated herein.

Preferred partially-oxidizing dyes are cationic triphenylmethane dyes, such as Basic Blue 7, Basic Blue 26, Basic Violet 2 and Basic Violet 14, aromatic systems, which are substituted with a quaternary nitrogen group, such as Basic Yellow 57, Basic Red 76, Basic Blue 99, Basic Brown 16 and Basic Brown 17, cationic anthraquinone dyes, such as HC Blue 16 (Bluequat B), as well as partially-oxidizing dyes comprising a heterocyclus, which has at least one quaternary nitrogen atom, more particularly Basic Yellow 87, Basic Orange 31 and Basic Red 51. The cationic partially-oxidizing dyes, which are sold under the trade name of Arianor, are also preferred cationic partially-oxidizing dyes as contemplated herein.

Suitable non-ionic substantive dyes are, in particular, non-ionic nitro and quinone dyes and neutral azo dyes. Preferred nonionic partially-oxidizing coloring agents are the compounds known under the international designations and/or trade name HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzol, 2-amino-4-nitrophenol, 1,4-bis-(2-hydroxyethyl)-amino-2-nitrobenzol, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzol, 1-amino-4-(2-hydroxyethyl)amino-5-chlor-2-nitrobenzol, 4-amino-3-nitrophenol, 1-(2'-Ureidoethyl)amino-4-nitrobenzol, 2-[(4-amino-2-nitrophenyl)amino]benzoic acid, 4-[(3-hydroxypropyl)amino]-3-nitrophenol, 4-nitro-o-phenylendiamine, 6-nitro-1,2,3,4-tetrahydrochinoxaline, 2-hydroxy-1,4-naphthoquinone, picramic acid and the salts thereof, 2-amino-6-chloro-4-nitrophenol, 4-ethylamino-3-nitrobenzoic acid and 2-chlor-6-ethylamino-4-nitrophenol are particularly preferred.

Oxidation Composition (B)

The hair's own dye melanin for blonding is decomposed by the influence of a peroxide compound as the oxidant. Hydrogen peroxide is typically used for this purpose. Hydrogen peroxide can be used only in the form of a hydrous solution.

Oxidant compositions (B) as contemplated herein are wherein they contain from about 0.5 to about 13 wt. %, preferably from about 1 to about 9 wt. %, more preferably from about 2 to about 7 wt. % and most preferably from about 3 to about 4.5 wt. % hydrogen peroxide (calculated as 100% H2O2), in each case relative to the total weight of the oxidation composition (B).

Blonding agents (A-2), which are able to achieve a dramatic lightening effect, for example for the blonding or lightening of very dark, melanin-rich keratin fibers, can also contain strongly oxidizing peroxide compounds such as potassium, sodium and/or ammonium persulfate and/or sodium percarbonate.

Water

The oxidation compositions (B) used as contemplated herein contain water, specifically in a quantity of from about 20 to about 95 wt. %, preferably from about 30 to about 90 wt. %, more preferably from about 40 to about 85 wt. %, most preferably from about 50 to about 80 wt. %, in each case relative to the total weight of the oxidation composition (B).

pH Value

Oxidant compositions (B) used as contemplated herein have a pH value in the range from about 2.5 to about 6.5, preferably in the range from about 3 to about 5.5, more particularly in the range from about 3.5 to about 5.0, in each case measured at about 20° C.

Gel-Forming Salt in the Oxidation Composition (B)

Insofar as the at least one salt of a polyvalent metal ion, selected from calcium, calcium-, strontium, barium and aluminum salts having a water solubility at about 20° C. of at least about 500 mg/l and, under certain conditions, from potassium salts having a water solubility at about 20° C. of at least about 500 mg/l, is included in the oxidation composition (B), preferably in a total quantity of from about 0.1 to about 5 wt. %, more preferably from about 0.2 to about 3 wt. %, most preferably from about 0.5 to about 2.5 wt. %, in each case relative to the weight of composition (B). Most preferably, the oxidation composition (B) comprises at least one salt d)i which, at about 20° C., has a water solubility of at least about 500 mg/l, preferably of at least about 40 g/l, more preferably of at least about 200 g/l, and most preferably of at least about 350 g/l. The preferred calcium chloride as contemplated herein has a water solubility of about 740 g/l at about 20° C. Other most preferred salts d)i as contemplated herein are selected from calcium acetate (water solubility of about 374 g/l), calcium lactate, calcium gluconate, calcium gluconate lactate. Aluminum chloride, aluminum hydroxychloride, aluminum sulfate, aluminum lactate, aluminum acetate, aluminum gluconate are likewise preferred. Potassium chloride, potassium acetate, potassium lactate, potassium gluconate and potassium sulfate are preferred for the gelling of kappa carragheenan, potassium, chloride, potassium lactate, and potassium gluconate being most preferred. Strontium chloride and barium chloride are also suitable. Preferably, mixtures of the aforementioned salts can also be contained. More preferably, the oxidation composition (B) comprises at least one salt, selected from calcium chloride, calcium actate, calcium gluconate and calcium gluconatlactate, as well as mixtures thereof in a total quantity of from about 0.1 to about 5 wt. %, more preferably from about 0.2 to about 3 wt.-%, most preferably from about 0.5 to about 2.5 wt. %, in each case relative to the weight of the composition (B). Most preferably, the oxidation composition (B) comprises from about 0.1 to about 5 wt. %, more preferably from about 0.2 to about 3 wt. %, most preferably from about 0.5 to about 2.5 wt. %, calcium chloride, in each case relative to the weight of the composition (B).

Organic Solvents

Moreover, all compositions used as contemplated herein, more particularly the oxidation compositions (B) and the blonding or lightening compositions (A-1), less preferably also (A-2), may contain at least one organic solvent, which is preferably selected from one or more mono- or polyvalent alcohols having from about 2 to about 9 carbon atoms, polyethylenglycols having from about 2 to about 20 ethylenglycol units, as well as mixtures of said solvents, preferably in a total quantity from about 0.001 to about 80 wt. %, more preferably from about 0.01 to about 50 wt. %, even more preferably from about 0.5 to about 20 wt. %, most preferably from about 1.5 to about 10 wt. %, in each case relative to the weight of the composition used as contemplated herein. Preferred organic solvents are selected from C1-C4-alcohols, more particularly ethanol and isopropanol, also selected from polyvalent alcohols having from about 2 to about 9, preferably selected from 1,2 propylenglycol, 2-methyl-1,3-propandiol, glycerine, butylenglycols such as 1,2 butylenglycol, 1,3-butylenglycol and 1,4 butylenglycol, pentylenglycols such as 1,2 pentandiol and 1,5 pentandiol, hexandiols such as 1,2 hexandiol and 1,6-hexandiol, hexantriols such as 1,2,6-hexantriol, 2-ethyl-2-hydroxymethyl-1,3-propandiol, dipropylenglycol, tripropylenglycol, diglycerin and triglycerine, and also selected from polyethylenglycols having from about 2 to about 20 ethylenglycol units, more particularly PEG-3, PEG-4, PEG-6, PEG-7, PEG-8, PEG-9, PEG-10, PEG-12, PEG-14, PEG-16, PEG-18 and PEG-20, as well as the mixtures thereof, PEG-3 to PEG-8 being preferred. The use of mixtures of the aforementioned substances is like preferred as contemplated herein.

Mixture Ratios (A) (B)

Moreover, for the blonding or lightening result, it is important for the ready-to-use blonding or lightening agent, which is obtained by mixing blonding or lightening composition (A) with an oxidation composition (B) used as contemplated herein, to have a pH value in the range of from about 6.5 to about 11.0, preferably from about 8 to about 10.5, more preferably from about 8.5 to about 9.5, in each case measured at about 20° C. At such pH values, the outer keratin fiber layer opens to the optimal extent to absorb the oxidant, and the oxidative effect of the hydrogen peroxide and possibly other peroxide compounds develops to the optimal extent.

It can also be preferred as contemplated herein for the ready-to-use blonding or lightening agent to be produced by mixing a lightening composition (A-1) as contemplated herein with a lightening composition (A-2) used as contemplated herein and an oxidation composition (B) used as contemplated herein.

Methods, preferably multi-tone color changing of keratinous fibers, preferred as contemplated herein, are therefore wherein the weight ratio of blonding agent (A) or lightening composition (B) is in the range of from about 1:10 to about 4:1, preferably in the range of from about 1:5 to about 3:1, more preferably in the range of from about 1:4 to about 2:1 and most preferably in the range of from about 1:2 to about 1:1.

In order to promote the miscibility of (A) and the ability of the lightening or blonding agent to be washed out of the keratin fibers at the end of the method as contemplated herein, it is preferred as contemplated herein for at least the blonding or lightening composition (A) to contain at least one surfactant, preferably in a total quantity of from about 0.1 to about 15 wt. %, preferably from about 1 to about 8 wt. %, relative to the weight of the composition (A).

The composition (B) also preferably comprises at least one surfactant, preferably in a total quantity of from about 0.1 to about 10 wt. %, preferably from about 1 to about 5 wt. %, relative to the weight of the composition (B).

Suitable surfactants, more particularly for (A) and (B), are non-ionic, anionic, cationic and amphoteric tensides. Non-ionic and anionic surfactants, as well as mixtures thereof, are preferred. Preferred anionic surfactants are alkyl sulfates, alkyl ether sulfates and ether carboxylic acids having from about 10 to about 18 C-atoms per alkyl group and up to about 12 glycol ether groups per molecule. Particularly preferred amphoteric surfactants are N-cocosalkylaminopropionate, cocosacylaminoethylaminopropionate and C12-C18 acylsarcosin.

Preferred non-ionic surfactants are selected from ethoxylated C10-C24 fatty alcohols having an ethoxylization degree of from about 4 to about 120, preferably from about 10 to about 50, more preferably from about 12 to about 20, wherein mixtures of said ethoxylated C10-C24 fatty alcohols with various degrees of ethoxylization are preferred. Other preferred non-ionic surfactants are selected from ethoxylated glycerinmono-, -di- and -triesters of C10-C24 fatty acids, for example PEG-40 Castor Oil, PEG-40 Hydrogenated Castor Oil, PEG-60 Castor Oil or PEG-60 Hydrogenated Castor Oil. Other preferred non-ionic surfactants are selected from C8-C22-alkylmono- and -oligoglycosides. C8-C22-alkylmono- and -oligoglycosides are known, commercially available surfactants and emulsifiers. They are produced in particular by converting glucose or oligosaccharides with primary alcohols having from about 8 to about 22 carbon atoms. With respect to the glycoside radical, both monoglycoside, wherein a cyclic sugar radical is glycosidically bound to the fatty alcohol, and also oligomer glycosides having an oligomerization degree to approx. 8, preferably from about 1 to about 2 are suitable. The degree of oligomerization is a statistical mean value, which is used as the basis of a homologous distribution typical for such technical products. Commercially-available products, which can be obtained for example under the trade name of Plantacare☐, contain a C8-C16-alkyl group glucosidically bound to an oligoglucoside radican, the mean oligomerization degree of which is from about 1 to about 2, more particularly from about 1,2 to about 1,4. Most preferred from about C8 to about C22-alkylmono- and -oligoglycosides are selected from octylglucoside, decylglucoside, lauryl glucoside, palmityl glucoside, isostearyl glucoside, stearyl glucoside, arachidyl glucoside and behenyl glucoside, as well as the mixtures thereof.

Preferred cationic surfactants include ammonium halogenides, more particularly chlorides and bromides, such as alkyltrimethylammoniumchlorides, dialkyldimethylammoniumchlorides and trialkylmethylammoniumchlorides, e.g. cetyltrimethylammoniumchloride, stearyltrimethylammoniumchloride, distearyldimethylammoniumchloride, lauryldimethylammoniumchlorides, lauryldimethylbenzylammoniumchloride and tricetylmethylammoniumchloride, as well as the imidazolium compounds known under the INCI trade names of Quaternium-27 and Quaternium-83.

Gelling Composition (C)

In order to produce the separating layer with a similar effect on the highlighting foils as contemplated herein or a water- and ammonia barrier layer from polysaccharide gel in-situ on the keratin fibers, a gel composition (C) is applied to the keratin fibers treated with the mixture of blonding or lightening composition (A) and oxidant composition (B), for example by means of a brush or similar applicator or—most preferred—by spraying, wherein the gel composition (C) contains:

c)i. from about 0.1 to about 3 wt. %, preferably from about 0.2 to about 2 wt. %, more preferably from about 0.4 to about 1 wt. %, relative to the weight of the composition (C), at least one salt of a multivalent metal ion, selected from calcium-, strontium-, barium- and aluminum salts having a water solubility at about 20° C. of at least about 500 mg/l, and also if the polysaccharide, which forms a gel with calcium ions, comprises kappa carragheenan or a salt thereof, the gelling composition (C) comprising from about 0.1 to about 3 wt. %, preferably from about 0.2 to about 2 wt. %, more preferably from about 0.4 to about 1 wt. %, relative to the weight of the composition (C), at least one salt, selected from potassium, calcium-, strontium-, barium- and aluminums salts having a water solubility at about 20° C. of at least about 500 mg/1, c)ii. from about 50 to about 99 wt. %, relative to the weight of the composition (C), water, c)iii. optionally at least one cation polymer, which is preferably selected from cationized guar ethers.

c)iv. wherein the gelling composition (C) has a pH value in the range from about 4 to about 12, preferably in the range of from about 4 to about 9, most preferably from about 6.5 to about 8, measured at about 20° C.;

Gel-Forming Salt/Water Solubility

At about 20° C., the at least one salt c)i has a water solubility of at least about 500 mg/l, preferably of at least about 40 g/l, more preferably of at least about 200 g/l, and most preferably of at least about 350 g/l. The preferred calcium chloride as contemplated herein has a water solubility of about 740 g/l at about 20° C. Other most preferred salts c)i as contemplated herein are selected from calcium acetate (water solubility of about 374 g/l), calcium lactate, calcium gluconate, calcium gluconate lactate. Aluminum chloride, aluminum hydroxychloride, aluminum sulfate, aluminum lactate, aluminum acetate, aluminum gluconate are likewise preferred. Potassium chloride, potassium acetate, potassium lactate, potassium gluconate and potassium sulfate are preferred for the gelling of kappa carragheenan, potassium, chloride, potassium lactate, and potassium gluconate being most preferred. Strontium chloride and barium chloride are also suitable. Preferably, mixtures of the aforementioned salts can also be contained.

The gelling composition (C) contains, in each case relative to its weight, from about 50 to about 99 wt. %, preferably from about 70 to about 95 wt. %, more preferably from about 75 to about 92 wt. % water.

The gelling composition (C) has a pH value in the range from about 4 to about 12, preferably in the range of from about 4 to about 9, more preferably from about 6.5 to about 8, measured at about 20° C. The setting of an acid or an alkali pH depends in part whether the viscosity of the composition (C) for improving the application characteristics thereof, more particularly the spray pattern, is to be increased by means of a thickening agent. Cationic polymers are particularly suitable for promoting moderate thickening of the composition (C). Preferred cationic polymers are selected from cationic guar derivatives, particularly from cationized guar ethers, more particularly from polymers having the INCI designations Hydroxypropyl Guar Hydroxypropyltrimonium Chloride and Guar hydroxypropyltrimonium Chloride. Insofar as the gelling composition (C) comprises a cationic polymer, said polymer is included in a total quantity of from about 0.01 to about 1 wt. %, preferably from about 0.1 to about 0.8 wt. %, more preferably from about 0.2 to about 0.5 wt. %, in each case relative to the weight of the composition (C). Insofar as the gelling composition (C) comprises a cationic polymer, said polymer preferably has a pH value in the range of from about 4 to about 6.5, measured at about 20° C.

Just like for the other compositions used as contemplated herein, the pH value is set by means of typical pH setting agents, more particularly citric acid, lactic acid, NaOH, KOH and similar cosmetically-tolerable acids and alkalis.

In a preferred embodiment of the lightening or blonding method as contemplated herein, the gelling composition (C) is produced in-situ or only from about 0.01 to about 24 hours before the method as contemplated herein is applied by mixing a solid, preferably powdery gelling composition (C'), comprising the at least one salt mentioned under d)i in powder form and optionally at least one cation polymer, which is preferably selected from cationized guar ethers, in powder form, with water d) iii, Most preferably, the gelling composition (C') additionally comprises a solid, preferably powdery, pH setting agent, e.g. an acid such as citric acid, and/or an alkalizing agent, such as sodium silicate.

Polysaccharide Composition (D)

A particularly preferred embodiment of the lightening or blonding agent as contemplated herein is wherein the at least one polysaccharide, which can form a gel with calcium ions in an aqueous medium and which is preferably selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts, is prepared in the form of a polysaccharide composition (D), comprising d)i. at least one polysaccharide, which can form a gel with calcium ions in hydrous medium and which is selected from alginic acid, kappa carragheenan, iota carragheenan and pectin, and/or at least one salt of the aforementioned polysaccharide, selected from the alkali metal-, ammonium-, mono-, di- and trialkyl ammonium-, mono-, di- and trialkanol ammonium- and magnesium salts, preferably in a total quantity of from about 0.1 to about 5 wt. %, preferably from about 0.5 to about 2 wt. %, more preferably from about 0.5 to about 2.5 wt. %, in each case relative to the weight of the composition (D), wherein in the case of the kappa carragheenan, the alkali metal salt is selected only from lithium- and sodium salts, d)ii. from about 50 to about 99.9, preferably from about 60 to about 95, more preferably from about 80 to about 90 wt. % water, in each case relative to the weight of the composition (D), d)iii. optionally at least one alkalizing agent, which is preferably selected from powdery sodium silicates, more particularly sodium meta silicates, d)iv. optionally at least one polymer, comprising (meth) acrylic acid-, (meth)acrylic acid-, (meth)acrylamide- and/or 2-acrylamido-2-methylpropane sulfonic acid monomers, preferably in a total quantity of from about 0.05 to about 3 wt. %, preferably from about 0.2 to about 0.5 wt. %, relative to the weight of the composition (D), d)v. optionally at least one oil in a total quantity of from about 0.1 to about 10 wt. %, preferably from about 0.3 to about 5 wt. %, more preferably from about 1 to about 3 wt. %, in each case relative to the weight of the polysaccharide composition (D), wherein optionally the polysaccharide composition (D) is produced by mixing a solid, preferably powdery, polysaccharide composition (D'), comprising d)i and optionally d)iii and/or optionally d)iv, with the component d)ii and optionally with the component d)v in situ or from about 0.01 to about 24 hours before applying the color-changing method as contemplated herein, In a preferred embodiment of the lightening or blonding method as contemplated herein, the polysaccharide composition (D) is produced in situ or from about 0.01 to about 24 hours before the color-changing method as contemplated herein is applied, by mixing a solid, preferably a powdery, polysaccharide composition (D'), comprising c)i and optionally c)iii and/or optionally c)iv, with the component c)ii and optionally with the component c)v.

For the in situ production of the polysaccharide composition (D), it has proven useful for at least one polysaccharide, which can form a gel with calcium iods in a hydrous medium, to be dissolved in about 25° C. to about 40° C. warm water comprising at least one oil in a total quantity of from about 0.1 to about 10 wt. %, preferably from about 0.3 to about 5 wt. %, most preferably from about 1 to about 3 wt. %, in each case relative to the weight of the polysaccharide composition (D). The oil ought to be included in the water before before the polysaccharide is added. This significantly accelerates the dissolution of the polysaccharide. Oils most preferred as contemplated herein are selected from natural and synthetic hydrocarbons, preferably from mineral oils, paraffin oils, C18-C30-isoparaffins, more particularly isoeicosan, polyisobutenes and polydecenes, also selected from C8-C16-isoparaffins, more particularly from isodecane, isododecane, isotetradecane and isohexadecane, as well as mixtures thereof, as well as 1,3-di-(2-ethylhexyl)-cyclohexane.

Other oils preferred as contemplated herein are selected from the esters of linear or branched saturated or unsaturated fatty alcohols with from about 2 to about 30 carbon atoms having linear or branched saturated or unsaturated fatty alcohols having from about 2 to about 30 carbon atoms which can be hydroxylated. This includes cetyl-2-ethylhexanoate, 2-hexyldecylstearate (e.g. Eutanol® G 16 S), 2-hexyldecyllaurate, isodecylneopentanoate, isononylisononanoate, 2-ethylhexylpalmitate (e.g. Cegesoft® C 24) and 2-ethylhexylstearate (e.g. Cetiol® 868). Preference is also given to isopropylmyristate, isopropylpalmitate, isopropylstearate, isopropylisostearate, isopropyloleate, isooctylstearate, isononylstearate, isocetylstearate, isononylisononanoate, isotridecylisononanoate, cetearylisononanoate, 2 ethylhexyllaurate, 2-ethylhexylisostearate, 2-ethylhexylcocoate, 2-octyldodecylpalmitate, butyloctanoic acid-2-butyloctanoate, diisotridecylacetate, n-butylstearate, n hexyllaurate, n decyloleate, oleyloleate, oleylerucate, erucyloleate, erucylerucate, ethylene glycoldioleate and ethylene glycoldipalmitate.

Additional oils preferred as contemplated herein are selected from the benzoic acid esters of linear or branched C8-22-alkanols. Particular preference is given to benzoic acid-C12-C15-alkyl esters, e.g. available as the commercial product Finsolv☐ TN, benzoic acid isostearyl esters, e.g. available as the commercial product Finsolv☐ SB, ethylhexylbenzoate, e.g. available as the commercial product Finsolv☐ EB, and benzoic acid octyldocecyl esters, e.g. available as the commercial product Finsolv☐ BOD.

Further oils as contemplated herein are selected from fatty alcohols having from about 6 to about 30 carbon atoms, which are unsaturated or branched and saturated or branched and unsaturated. The branched alcohols are often also referred to as Guerbet alcohols, as they are obtained by the Guerbet reaction. Preferred alcohols are 2-hexyldecanole (Eutanol® G 16), 2-octyldodecanole (Eutanol® G), 2-ethylhexyl alcohol and isostearylalcohol.

Further preferred oils are selected from Guerbet alcohols and Guerbet alcohol esters, e.g. from the commercial product Cetiol® PGL (2-Hexyldecanol and 2-Hexyldecyllaurat).

Additional cosmetic oils preferred as contemplated herein are selected from the triglycerides (=triple esters of glycerin) of linear or branched, saturated or unsaturated, if applicable hydroxylated C8 30 fatty acids, if they are liquid at about 20° C. Particular preference is given to the use of natural oils, such as amaranthus seed oil, apricot kernel oil, arganil, avocado oil, babassu oil, cotton seed oil, borage oil, camel oil, safflower oil, peanut oil, grenadine core oil, grapefruit seed oil, hemp oil, hazelnut oil, hollowseed oil, currant seed oil, jojoba oil, linseed oil, macadamia nut oil, corn oil, almond oil, manila oil, evening primrose oil, olive oil, palm oil, palm kernel oil, parannut oil, pectic oil, peach kernel oil, rapeseed oil, castor oil, sandalwood oil, sanddornkernel oil, sesame oil, soya oil, sunflower oil, grapeseed oil, walnut oil, wild-type oil, wheat germ oil, and the liquid fractions of coconut oil and the like. However, preference is also given to synthetic triglyceride oils, particularly capric/caprylic triglycerides, i.e. the commercial products Myritol® 318, Myritol® 331 (BASF) or Miglyol® 812 (Hüls) having unbranched fatty acid esters and glyceryl triisostearin with branched fatty acids.

Additional particularly preferred cosmetic oils as contemplated herein are selected from the dicarboxylic acid esters of linear or branched C2-C10 alkanols, particularly diisopropyl adipate, di-n-butyl adipate, di (2-ethylhexyl)) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Additional preferred cosmetic oils as contemplated herein are selected from the adducts of from about 1 to about 5 propylene oxide units on mono- or multivalent C8 22 alkanols, such as octanol, decanol, decanediol, lauryl alcohol, myristyl alcohol and stearyl alcohol, e.g. PPG-2 myristyl ether and PPG-3 myristyl ether (e.g. Witconol® APM).

Additional preferred cosmetic oils as contemplated herein are selected from the adducts of at least about 6 ethylene oxide and/or propylene oxide units on mono- or polyvalent C3-22 alkanols, such as glycerin, butanol, butanediol, myristyl alcohol and stearyl alcohol, which can be optionally esterified, such as PPG-14 butyl ether (Ucon Fluid® AP), PPG-9 butyl ether (e.g. Breox® B25), PPG-10 butanediol (Macol® 57), PPG-15 stearyl ether (Arlamol® E) and glycereth-7-diisononanoate.

Additional preferred cosmetic oils as contemplated herein are selected from the C8-C22 fatty alcohol esters of monovalent or multivalent C2-C7 hydroxy carboxylic acids, particularly the esters of glycolic acid, lactic acid, malic acid, tartaric acid, citric acid and salicylic acid. Such esters based on linear C14/15 alkanols, such as C12-C15 alkyl lactate, and on C12/13 alkanols branched in 2 position are commercially available under the trade name Cosmacol☐ from Nordmann Rassmann GmbH & Col, Hamburg, particularly the commercial products Cosmacol☐ ESI, Cosmacol☐ EMI and Cosmacol☐ ETI.

Additional preferred cosmetic oils as contemplated herein are selected from the symmetrical, asymmetrical or cyclical esters of carboxylic acid with C3-22 alkanols, C3-22 alkanediols or C3-22 alkanetriols, e.g. dicaprylylcarbonate (Cetiol® CC) or the esters according to the teaching of DE 19756454 A1, particularly glycerin carbonate.

Additional cosmetic oils that can be preferred as contemplated herein are selected from the esters of dimeric unsaturated C12 C22 fatty acids (dimeric fatty acids) with monovalent linear, branched or cyclical C2-C18 alkanols or multivalent linear and branched C2 C6 alkanols.

Additional cosmetic oils that are suitable as contemplated herein are selected from the silicone oils, which include, for example, dialkyl- and akylaryl siloxanes, such as cyclopentadienyl, cyclohexsiloxane, dimethylpolysiloxane and methylphenylpolysiloxane, but also hexamethyldisiloxane, octamethyltrisiloxane and decamethyltetrasiloxane. Preference can be given to volatile silicone oils which can be cyclic, such as octamethylcyclotetrasiloxane, decamethylcyclopentasiloxane and dodecamethylcyclohexsiloxane, and mixtures thereof, as are contained, for example, in the commercial products DC 244, 245, 344 and 345 of Dow Corning. Volatile silicone oils are also suitable, particularly hexamethyldisiloxane (L2), octamethyltrisiloxane (L3), decamethyltetrasiloxane (L4) and any double and trouble mixtures of L2, L3 and/or L4, preferable such mixtures which are commercially available, for example, in the products DC 2-1184, Dow Corning® 200 (0.65 cSt) and Dow Corning® 200 (1.5 cSt) from Dow Corning. Preferred nonvolatile silicone oils are selected from higher molecular linear dimethylpolysiloxanes, commercially available, for example, under the name Dow Corning® 200 Fluid with kinematic viscosities (25° C.) in a range of from about 5 to about 100 cSt, preferably from about 5 to about 50 cSt or also from about 5 to about 10 cSt, and dimethylpolysiloxane with a kinematic viscosity (about 25° C.) of approximately 350 cSt. As contemplated herein, the use of mixtures of the aforementioned oils is most preferred.

The dissolution of the polysaccharide can also be promoted by adding a surfactant, for example in a total quantity of from about 0.05 to about 3 wt. %, preferably from about 0.1 to about 1 wt. %, more preferably from about 0.3 to about 0.8 wt. %, relative to the weight of the composition (D). However, a surfactant can cause the polysaccharide composition (D), which ought to be shaken to loosen the polysaccharide, to foam too strongly, making it difficult to apply. The polysaccharide composition (D) therefore preferably comprises no surfactant.

Most preferably used polysaccharide compositions (D) and (D') are wherein the at least one polysaccharide, which can form a gel with calcium ions in hydrous medium, is selected from alginic acid, sodium alginate, ammonium alginate, magnesium alginate, monoethanolammoniumalginate, kappa carragheenan, the lithium salt of kappa carragheenan, the sodium salt of kappa carragheenan, iota carragheenan, the lithium salt of iota carragheenan, the sodium salt of iota carragheenan, the potassium salt of iota carragheenan, the ammonium salt of iota carragheenan, pectin, sodium pectinate, ammonium pectinate, potassium pectinate and magnesium pectinate, as well as mixtures of said substances. Most preferred mixtures as contemplated herein are those from alginic acid and sodium alginate, more particularly mixtures from alginic acid and sodium alginate in the weight ratio of alginic acid to sodium alginate in the range of from about 1:2 to about 2:1, preferably in the range from about 0.8 to about 1.25, most preferably in the weight ratio of about 1:1.

Most preferably, the polysaccharide composition (D) comprises a mixture of alginic acid and sodium alginate in a total quantity of from about 0.1 to about 5 wt. %, more preferably from about 0.2 to about 3 wt. %, most preferably from about 0.5 to about 2.5 wt. %, in each case relative to the weight of the composition (D), wherein the a weight ratio of alginic acid to sodium alginate is preferably in the range of from about 1:2 to about 2:1, more preferably in the range from about 0.8 to about 1.25, most preferably in the weight ratio of about 1:1.

As contemplated herein, the polysaccharide composition (D) has a pH value in the range from about 7 to about 12, preferably in the range from about 8 to about 10, most preferably about 8.5 to about 9.5, measured at about 20° C. Therefore, the polysaccharide composition (D) preferably comprises at least one alkalizing agent, which is preferably selected from powdery sodium silicates, more preferably powdery sodium meta silicates. The other aforementioned alkalizing agents can also be used to set the pH value of the polysaccharide composition (D). For the polysaccharide composition (D'), a content of at least one solid, preferably powdery, alkalizing agent is preferred, which is preferably selected from powdery sodium silicates, more particularly powdery sodium meta silicates.

As contemplated herein, it may be preferable for the polysaccharide composition (D) polysaccharide composition (D') to contain at least one polymer, comprising (meth) acrylic acid, (meth)acrylate-, (meth)acrylamide- and/or 2-acrylamido-2-methylpropansulfonic acid monomers, preferably in a total quantity of from about 0.05 to about 3 wt. %, more preferably from about 0.2 to about 0.5 wt. %, relative to the weight of the composition (D), The addition of said polymers serves primarily to improve the solubility of the polysaccharide during the in situ production of the composition (D). Preferably, the at least one polymer, comprising (meth)acrylic acid (meth)acrylate-, (meth)acrylamide- and/or 2-acrylamido-2-methylpropansulfonic acid monomers, is selected from cross-linked homopolymers of the acrylic acid, cross-linked homopolymers of 2-acrylamido-2-methylpropansulfonic acid, cross-linked copolymers comprising acrylic acid- and 2-acrylamido-2-methylpropansulfonic acid units, cross-linked copolymers comprising 2-methyl-2[(1-oxo-2-propenyl)amino]-1-propansulfonic acid units and hydroxyethylacrylate units, cross-linked copolymers comprising acrylamide- and 2-acrylamido-2-methylpropansulfonic acid units, cross-linked copolymers comprising methacrylic acid units and C1-C4-alkylacrylate units, cross-linked copolymers comprising acrylic acid units and C1-C4-alkylmethacrylate units, as well as mixtures thereof.

Most preferably, the at least one polymer, comprising (meth)acrylic acid-, (meth)acrylate-, (meth)acrylamide- and/or 2-acrylamido-2-methylpropansulfonic acid monomers, having no monomers, which are substituted with possibly ethoxylated, C6-C24-alkyl- or C6-C24-alkenyl groups;

A further lightening or blonding method as contemplated herein is wherein said method is applied with at least a second blonding or lightening agent (A'), (A"), (A''') etc. instead of (A), wherein compositions (A) and (A'), (A"), (A''') etc. differ from one another in terms of quality and/or quantity, at least with respect to the partially-oxidizing hair dyes included therein.

For all embodiments of the present lightening or blonding method preferred as contemplated herein, it is also most preferable for the keratin fiber strands not be provided with solid, flat separating aids, more particularly not with foils from solid materials such as aluminum, paper or Styrofoam.

Another subject matter of the present disclosure is a kit for lightening and/or blonding keratinous fibers, comprising the following components (D) and (C), as well as optionally (A) and optionally (B), which are physically separated from one another:

I. A polysaccharide composition (D), comprising
d)i. at least one polysaccharide, which can form a gel with calcium ions in an aqueous medium and which is preferably selected from alginic acid, kappa carragheenan, iota carragheenan and pectin, and/or at least one salt of the aforementioned polysaccharides, selected from the alkali metal-, ammonium-, mono-, di- and trialkyl ammonium-, mono-, di- and trialkanolammonium- and magnesium salts, wherein in the case of salts of the kappa carragheenan, the alkali metal salt thereof is selected only from lithium- and sodium salts, mixtures of alginic acids and sodium alginate being most preferred, d)ii. at least one alkalizing agent, preferably selected from powdery sodium silicates, most particularly powdery sodium meta silicates, d)iii. optionally at least one polymer comprising (meth) acrylic acid-, (meth)acrylic acid ester-, (meth)acrylamide- and/or 2-acrylamido-2-methylpropansulfonic acid monomers, which preferably has no monomers and which can be substituted with ethoxylated, C6-C24-alkyl- or C6-C24-alkenyl groups;

II. a gelling composition (C'), comprising c)i. at least one salt of a polyvalent metal ion selected from calcium-, strontium-, barium- and aluminum salts having a water solubility at about 20° C. of at least about 500 mg/l, and also if the polysaccharide, which forms a gel with calcium ions, comprises kappa carragheenan or a salt thereof, at least one salt selected from potassium-, calcium-, strontium-, barium- and aluminum salts having a water solubility at about 20° C. of at least about 500 mg/l;

c)ii. optionally at least one cation polymer, which is preferably selected from cationized guar ethers.

III. optionally a blonding or lightening composition (A), comprising a)i at least one alkalizing agent, a)ii optionally at least one consistency enhancer and a)iii optionally at least one solvent, selected from water, one or more mono- or polyvalent alcohols having from about 2 to about 9 carbon atoms, as well as mixtures of said solvents, and a)iv optionally at least one partially-oxidizing dye, wherein the blonding or lightening composition (A), insofar as, relative to its weight, it comprises more than about 7 wt. % water, has a pH value in the range of from about 6.0 to about 11.5, measured at about 20° C. and, insofar as the composition (A), relative to its weight, comprises from about 0 to about 7 wt. % water, it's about 30 wt. % dispersion in water has a pH value in the range of from about 6.0 to about 12.0, preferably from about 7.5 to about 11.5, more preferably from about 8 to about 11.0, in each case measured at about 20° C.; IV. optionally an oxidant composition (B), comprising b)i. from about 1 to about 18 wt. % hydrogen peroxide, relative to the weight of the composition (B), and b)ii. water, b)iii. wherein the oxidant composition (B) has a pH value in the range from of from about 2.5 to about 6.5, preferably in the range from about 3 to about 5.5, more particularly in the range from about 3.5 to about 5.0, in each case measured at about 20° C.

For kits as contemplated herein, the statements made above on the lightening and blonding method as contemplated herein apply mutatis mutandis.

Preferred kits as contemplated herein have the advantage that the essential ingredients of the compositions (C) and (D) can be commercialized in a space- and packaging-saving manner, for example is sachets, which preferably have a vapor-impermeable layer. For example, the hairdresser can produce the compositions (C) and (D) themselves simply by mixing the compositions (C') and (D') with water and/or an oily hair care composition. Preferably, the kit also comprises instructions for use for applying the lightening and blonding method preferred as contemplated herein.

Another subject matter of the present disclosure is the use of at least one polysaccharide salt, selected from calcium alginate, potassium kappa carragheenat, calcium kappa carragheenat, calcium iota carragheenat, calcium pectinate, aluminum alginate, aluminum kappa carragheenat, aluminum iota carragheenat, aluminum pectinate, strontium alginate, strontium kappa carragheenat, strontium iota carragheenat, strontium pectinate, barium alginate, barium kappa carragheenat, barium iota carragheenat, barium pectinate, as well as mixtures of said polysaccharide salts, for coating keratinous fiber sections or keratinous fiber strands in a method for lightening and/or blonding keratinous fibers, wherein the lightening and/or blonding method is preferably a method according to claim 1.

For this use and preferred embodiments as contemplated herein, the statements made above on the lightening and blonding methods and kits as contemplated herein apply mutatis mutandis.

Another subject matter of the present disclosure is the use of at least one polysaccharide salt, selected from calcium alginate, potassium kappa carragheenat, calcium kappa carragheenat, calcium iota carragheenat, calcium pectinate, aluminum alginate, aluminum kappa carragheenat, aluminum iota carragheenat, aluminum pectinate, strontium alginate, strontium kappa carragheenat, strontium iota carragheenat, strontium pectinate, barium alginate, barium kappa carragheenat, barium iota carragheenat, barium pectinate, as well as mixtures of said polysaccharide salts, in a method for lightening and/or blonding keratinous fibers in the presence of ammonium hydroxide or an ammonium salt, wherein the lightening and/or blonding method is preferably a method according to claim 1 for reducing the ammonia release and/or for reducing the drying of the lightening and/or blonding composition.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for lightening keratinous fibers, the method comprising:
   a) preparing a lightening composition (A), containing:
      a1) at least one alkalizing agent;
      a2) optionally at least one consistency enhancer; and
      a3) optionally at least one solvent, selected from water and at least one organic solvent; and
      a4) optionally at least one partially-oxidizing hair dye; wherein when the lightening composition (A), relative to its weight, contains more than about 7 wt. % water, the lightening composition (A) has a pH value of from about 6.0 to about 11.5, measured at about 20° C.,
      and wherein when the lightening composition (A), relative to its weight, contains from about 0 to about 7 wt. % water, a 30 wt. % dispersion of the lightening composition (A) in water has a pH value of from about 6.0 to about 12.0, measured at about 20° C.;
   b) preparing an oxidant composition (B), containing:
      b1) from about 1 to about 18 wt. % hydrogen peroxide, relative to the weight of the composition (B); and
      b2) water; wherein the oxidant composition (B) has a pH value of from about 2.5 to about 6.5, measured at about 20° C.;

c) preparing a polysaccharide composition (D), containing:
  c1) at least one polysaccharide adapted to form a gel with calcium ions in a hydrous medium and selected from alginic acid; iota carragheenan; pectin; at least one alkali metal salt of alginic acid, iota carragheenan, and pectin selected from ammonium salt, mono-, di- and trialkyl ammonium salt, mono-, di- and trialkanol ammonium salt, and magnesium salt; kappa carragheenan; and/or at least one alkali metal salt of kappa carragheenan selected from lithium salt and sodium salt; and
  c2) from about 50 to about 99.9 wt. % water, relative to the weight of the polysaccharide composition (D);
  c3) optionally at least one alkalizing agent;
  c4) optionally at least one polymer, containing (meth)acrylic acid monomers, (meth)acrylic acid monomers, (meth)acrylamide monomers and/or 2-acrylamido-2-methylpropane sulfonic acid monomers;
  c5) optionally at least one oil in a total quantity of from about 0.1 to about 10 wt. % relative to the weight of the polysaccharide composition (D); then
d) producing a mixture (M) of the lightening composition (A) and the oxidant composition (B), wherein the mixture (M) has a pH value of from about 6.0 to about 11, measured at about 20° C.;
e) applying at least one partial quantity of the mixture (M) on a first plurality of selected keratinous fibers;
f) applying the polysaccharide composition (D) to the first plurality of selected keratinous fibers for a duration of from about 0.1 to about 60 minutes;
g) rinsing the first plurality of keratinous fibers with water and, optionally, a cleaning agent; and
h) optionally post-treating the first plurality of selected keratinous fibers with a conditioning agent and drying the first plurality of selected keratinous fibers;
  wherein the method further includes applying at least one salt, not contained in the polysaccharide composition (D), of a polyvalent metal ion selected from calcium salt, strontium salt, barium salt and aluminum salt having a water solubility at 20° C. of at least about 500 mg/l, and, if ci) the polysaccharide comprises kappa carragheenan or one of the salts thereof, applying at least one salt, not contained in the polysaccharide composition (D), selected from potassium salt, calcium salt, strontium salt, barium salt and aluminum salt having a water solubility at 20° C. of at least about 500 mg/I, and wherein applying the at least one salt includes applying the at least one salt to the first plurality of selected keratinous fibers.

2. The method of claim 1 wherein a3) the at least one solvent is selected from water and one or more monovalent or polyvalent alcohols having from about 2 to about 9 carbon atoms, polyethylenglycols having from about 2 to about 20 ethylenglycol units, and mixtures thereof.

3. The method of claim 1 wherein the polysaccharide composition (D), relative to its weight, contains from about 0.1 to about 5 wt. % of c1) the at least one polysaccharide.

4. The method of claim 1 wherein the polysaccharide composition (D), relative to its weight, contains from about 60 to about 95 wt. % water.

5. The method of claim 1 wherein c3) the at least one alkalizing agent is a sodium meta silicate.

6. The method of claim 1 wherein c) preparing the polysaccharide composition (D) comprises mixing a solid polysaccharide composition (D'), containing c1) and optionally c3) and/or optionally c4), with c2) and optionally with c5) in situ or from about 0.01 to about 24 hours before applying the polysaccharide composition (D) to the keratin fiber section(s) treated with (M) or the keratin fiber ensemble treated with mixture (M).

7. The method of claim 1 wherein the lightening composition (A) contains, relative to the weight of the composition (A), from about 0.1 to about 3 wt. % of at least one salt of a polyvalent metal ion, selected from calcium salt, strontium salt, barium salt and aluminum salt having a water solubility at 20° C. of at least about 500 mg/l, and, if c1) the polysaccharide comprises kappa carragheenan or one of the salts thereof, the lightening composition (A) contains, relative to the weight of the composition (A), from about 0.1 to about 3 wt. % of at least one salt, selected from potassium, calcium salt, strontium salt, barium salt and aluminums salt having a water solubility at 20° C. of at least about 500 mg/l.

8. The method of claim 1 wherein the oxidant composition (B) contains, relative to the weight of the oxidant composition (B), from about 0.1 to about 3 wt. % of at least one salt of a polyvalent metal ion, selected from calcium salt, strontium salt, barium salt and aluminum salt having a water solubility at 20° C. of at least about 500 mg/1, and, if c1) the polysaccharide comprises kappa carragheenan or one of the salts thereof, the oxidant composition (B) contains, relative to the weight of the oxidant composition (B), from about 0.1 to about 3 wt. % of at least one salt, selected from potassium, calcium salt, strontium salt, barium salt and aluminums salt having a water solubility at 20° C. of at least about 500 mg/l.

9. The method of claim 1 further comprising:
producing a gel composition (C) containing:
  d1) from about 0.1 to about 3 wt. %, relative to the weight of the gel composition (C), of at least one salt of a polyvalent metal ion, selected from calcium salt, strontium salt, barium salt and aluminum salt having a water solubility at 20° C. of at least about 500 mg/1, and, if c1) the polysaccharide comprises kappa carragheenan or one of the salts thereof, the gel composition (C) contains, relative to the weight of the gel composition (C), from about 0.1 to about 3 wt. % of at least one salt, selected from potassium, calcium salt, strontium salt, barium salt and aluminums salt having a water solubility at 20° C. of at least about 500 mg/1;
  d2) from about 50 to about 99 wt. %, relative to the weight of the gel composition (C), water;
  d3) optionally at least one cation polymer;
wherein the gel composition (C) has a pH value of from about 4 to about 12, measured at 20° C.;
wherein the gelling composition (C) is optionally produced in-situ or from about 0.01 to about 24 hours before preparing a lightening composition (A) by mixing a solid gel composition (C') containing d1) the at least one salt in powder form and optionally at least one cation polymer, in powder form, with d3) water;
wherein the method comprises:
applying the gel composition (C) after e) applying the mixture (M) on the first plurality of selected keratinous fibers and before applying the polysaccharide composition (D) to the first plurality of selected keratinous fibers;
adding the gel composition (C) to composition (A), to composition (B), or to mixture (M) before e) applying the mixture (M) on the first plurality of selected keratinous fibers; or applying the gel composition (C) after applying the polysaccharide composition (D) to the first plurality of selected keratinous fibers.

10. The method of claim 9 wherein the weight ratio of lightening composition (A) to oxidant composition (B) is from about 1:10 to about 4:1.

11. The method of claim 9 wherein the weight ratio of gel composition (C) to mixture (M) of lightening composition (A) and oxidant composition (B) is from about 1:20 to about 1:2.

12. The method of claim 9 wherein the weight ratio of polysaccharide composition (D) to mixture (M) of lightening composition (A) and oxidant composition (B) is from about 1:20 to about 1:2.

13. The method of claim 9 wherein the weight ratio of polysaccharide composition (D) to gel composition (C) is from about 0.2:1 to about 2:1.

14. The method of claim 1 wherein the first plurality of selected keratinous fibers are not provided with solid, flat separating aids.

15. The method of claim 1 wherein c4) the at least one polymer is selected from cross-linked homopolymers of the acrylic acid, cross-linked homopolymers of 2-acrylamido-2-methylpropansulfonic acid, cross-linked copolymers consisting of acrylic acid units and 2-acrylamido-2-methylpropansulfonic acid units, cross-linked copolymers consisting of 2-methyl-2[(1-oxo-2-propenyl)amino]-1-propansulfonic acid units and hydroxyethylacrylate units, cross-linked copolymers consisting of acrylamide- and 2-acrylamido-2-methylpropansulfonic acid units, cross-linked copolymers consisting of methacrylic acid units and C1-C4-alkylacrylate units, cross-linked copolymers consisting of acrylic acid units and C1-C4-alkylmethacrylate units, and mixtures thereof.

16. A kit for lightening keratinous fibers comprising:
a polysaccharide composition (D), comprising:
  d1) at least one polysaccharide adapted to form a gel with calcium ions in a hydrous medium and selected from alginic acid; iota carragheenan; pectin; at least one alkali metal salt of alginic acid, iota carragheenan, and pectin selected from ammonium salt, mono-, di- and trialkyl ammonium salt, mono-, di- and trialkanol ammonium salt, and magnesium salt; kappa carragheenan; and/or at least one alkali metal salt of kappa carragheenan selected from lithium salt and sodium salt;
  d3) at least one alkalizing agent; and
  d4) optionally at least one polymer containing (meth)acrylic acid monomers, (meth)acrylic acid ester monomers, (meth)acrylamide- and/or 2-acrylamido-2-methylpropansulfonic acid monomers, wherein the at least one polymer is unsubstituted or is substituted with ethoxylated, C6-C24-alkyl- or C6-C24-alkenyl groups
a gel composition (C") comprising:
  c1) at least one salt of a polyvalent metal ion, selected from calcium salt, strontium salt, barium salt and aluminum salt having a water solubility at 20° C. of at least about 500 mg/l, and, if d1) the polysaccharide comprises kappa carragheenan or one of the salts thereof, at least one salt, selected from potassium, calcium salt, strontium salt, barium salt and aluminums salt having a water solubility at 20° C. of at least about 500 mg/l; and
  c2) optionally at least one cation polymer;
wherein the gel composition (C) has a pH value of from about 4 to about 12, measured at 20° C.;
optionally a lightening composition (A), comprising:
  a1) at least one alkalizing agent;
  a2) optionally at least one consistency enhancer;
  a3) optionally at least one solvent, selected from water, one or more mono- or polyvalent alcohols having from about 2 to about 9 carbon atoms, and mixtures thereof; and
  a4) optionally at least one partially-oxidizing hair dye;
wherein when the lightening composition (A), relative to its weight, contains more than about 7 wt. % water, the lightening composition (A) has a pH value of from about 6.0 to about 11.5, measured at about 20° C., and
wherein when the lightening composition (A), relative to its weight, contains from about 0 to about 7 wt. % water, a 30 wt. % dispersion of the lightening composition (A) in water has a pH value of from about 6.0 to about 12.0, measured at about 20° C.; and
optionally an oxidant composition (B), comprising:
  b1) from about 1 to about 18 wt. % hydrogen peroxide, relative to the weight of the composition (B); and
  b2) water;
wherein the oxidant composition (B) has a pH value of from about 2.5 to about 6.5, measured at about 20° C.;
wherein the components (D), (C), (A), if present, and (B), if present, are physically separated from one another.

* * * * *